United States Patent [19]

Kukolja et al.

[11] 4,048,162

[45] Sept. 13, 1977

[54] PROCESS FOR PREPARING 3-HYDROXY CEPHALOSPORINS

[75] Inventors: Stjepan Kukolja; Charles F. Murphy, both of Indianapolis, Ind.

[73] Assignee: Eli Lilly and Company, Indianapolis, Ind.

[21] Appl. No.: 626,683

[22] Filed: Oct. 29, 1975

[51] Int. Cl.$^2$ .................. C07D 501/02; C07D 501/08
[52] U.S. Cl. .................................. 544/22; 124/246; 544/23
[58] Field of Search ............................ 260/243 C

[56] References Cited

U.S. PATENT DOCUMENTS 3,872,086  3/1975  Barton et al. .................. 260/243 C

*Primary Examiner*—Nicholas S. Rizzo
*Attorney, Agent, or Firm*—William C. Martens, Jr.; Everet F. Smith

[57] ABSTRACT

3-Hydroxycephalosporins are prepared by treating a 3-hydroxy-4-bromo-2-(2-formylthio-4-oxo-3-amido or imido-1-azetidinyl)-2-butenoate ester with 1,5-diazabicyclo[3.4.0]non-5-ene (DBN) or 1,5-diazabicyclo[5.4.0]undec-5-ene (DBU) at a temperature of from about 0° C. to about 25° C.

10 Claims, No Drawings

PROCESS FOR PREPARING 3-HYDROXY CEPHALOSPORINS

BACKGROUND OF THE INVENTION

This invention relates to a new process for the preparation of 3-hydroxycephalosporins. These compounds are disclosed and claimed in U.S. Pat. No. 3,917,587. The process disclosed in the copending application for preparing 3-hydroxycephalosporins involves treatment of a 3-exomethylenecepham compound with ozone to form an intermediate ozonide followed by decomposition of the ozonide in the presence of a reducing compound to produce the desired 3-hydroxycephalosporin.

The novel process for preparing 3-hydroxycephalosporins by this invention comprises ring-closure of 3-hydroxy-4-bromo-2-(2-formylthio-4-oxo-3-amido-1-azetidinyl)-2-butenoate esters or their corresponding 3-imido compounds. These compounds are alternatively named as azetidinones and, as such, can also be called 1-(1-protected carboxy-2-hydroxy-3-bromo-1-propenyl)-3-amido(or imido)-4-formylthioazetidin-2-ones.

The ring-closure reaction described herein is accomplished by treating the above butenoate esters with 1,5-diazabicyclo[3.4.0]non-5-ene (DBN) or 1,5-diazabicyclo[5.4.0]undec-5-ene (DBU).

SUMMARY OF THE INVENTION

This invention relates to a process for preparing a 3-hydroxycephalosporin of the formula

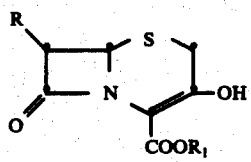

which comprises reacting a butenoate ester compound of the formula

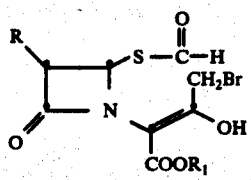

with an amine selected from the group consisting of 1,5-diazabicyclo[5.4.0]undec-5-ene and 1,5-diazabicyclo[3.4.0]non-5-ene at a temperature of from about 0° C. to about 25° C., in which, in the above formulae, $R_1$ is a carboxylic acid protecting group, and R is a. phthalimido;
b. an amido group of the formula

in which $R_2$ is
1. hydrogen, $C_1$-$C_3$ alkyl, halomethyl, thienyl-2-methyl, 4-protected-amino-4-protected carboxybutyl, benzyloxy, 4-nitrobenzyloxy, t-butyloxy, 2,2,2-trichloroethoxy, 4-methoxybenzyloxy;

2. a group of the formula $R'$—$(O)_m$—$CH_2$— in which m is 0 or 1, and $R'$ is phenyl or phenyl substituted with 1 or 2 halogens, protected hydroxy, nitro, cyano, trifluoromethyl, $C_1$-$C_4$ alkyl, or $C_1$-$C_2$ alkoxy;
3. a group of the formula

in which $R'$ is as defined above and W is protected hydroxy, protected carboxy, or protected amino; or c. an imidazolidinyl group of the formula

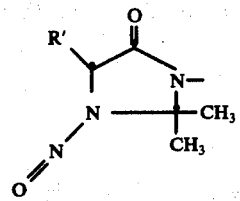

in which $R'$ is as defined above.

DETAILED DESCRIPTION OF THE INVENTION

As delineated hereinabove, the process of this invention is directed to the preparation of 3-hydroxycephalosporins of the formula

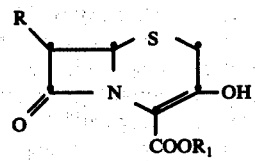

from compounds of the formula

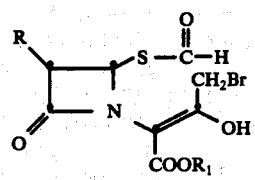

$R_1$ in the above formulae denotes a carboxylic acid protecting group, and, preferably, one which is removable by acid treatment or by hydrogenation. Preferred carboxylic acid protecting groups include, for example, $C_4$-$C_6$ tert-alkyl, 2,2,2-trihaloethyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, phenacyl, or p-halophenacyl, in any of the above of which halo denotes chlorine, bromine, or iodine.

Specific illustrations of the preferred carboxylic acid protecting groups which can be employed in the process of this invention include, for example, t-butyl, t-amyl, t-hexyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like.

Highly preferred carboxylic acid protecting groups are t-butyl, benzyl, p-nitrobenzyl, p-methoxybenzyl, benzhydryl, and 2,2,2-trichloroethyl.

R represents the substituent which is present in the 7-position of the 3-hydroxycephalosporin product of the process of this invention. R can be any of three possibilities or classes of possibilities. Of course, the structure of the R group in the 3-hydroxycephalosporin prepared by the process of this invention will depend upon and be identical to the structure of R in the 3-position of the azetidinyl moiety of the 2-butenoate ester starting material, which, in turn, normally will correspond to the structure of its usual precursor, a matter which is developed hereinafter.

First, R can be an imido function, specifically phthalimido.

Secondly, R can be an amido function of the formula

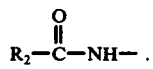

Specific illustrations of the group $R_2$ include, for example, hydrogen, methyl, ethyl, n-propyl, isopropyl, chloromethyl, bromomethyl, thienyl-2-methyl, 4-acetamido-4-p-nitrobenzyloxycarbonylbutyl, benzyloxy, 4-nitrobenzyloxy, t-butyloxy, 2,2,2-trichloroethoxy, 4-methoxybenzyloxy, benzyl, 3-bromobenzyl, 2,5-dichlorobenzyl, 4-chloroacetoxybenzyl, 2-nitrobenzyl, 3-cyanobenzyl, 4-trifluoromethylbenzyl, 3-methylbenzyl, 4-n-butylbenzyl, 2-methoxybenzyl, 3-ethoxybenzyl, phenoxymethyl, 3-iodophenoxymethyl, 4-fluorophenoxymethyl, 3-benzyloxyphenoxymethyl, 4-benzhydryloxyphenoxymethyl, 3-trityloxyphenoxymethyl, 4-nitrobenzyloxyphenoxymethyl, 3-nitrophenoxymethyl, 4-cyanophenoxymethyl, 2-trifluoromethylphenoxymethyl, 3-methylpheoxymethyl, 4-n-propylphenoxymethyl, 4-n-butylphenoxymethyl, 3-methoxyphenoxymethyl, 4-ethoxyphenoxymethyl, α-benzhydryloxybenzyl, α-(4-methoxybenzyloxy)benzyl, α-(2,2,2-trichloroethoxycarbonylamino)benzyl, α-(benzyloxy)-4-bromobenzyl, α-(benzhydryloxycarbonyl)-3-chlorobenzyl, α-(4-nitrobenzyloxycarbonylamino)-4-fluorobenzyl, α,4-di(formyloxy)benzyl, α-(4-nitrobenzyloxycarbonyl)-3-chloroacetoxybenzyl, α-(4-methoxybenzyloxycarbonylamino)-4-benzhydryloxybenzyl, α-benzyloxy-3-nitrobenzyl, α-(4-nitrobenzyloxycarbonyl)-2-cyanobenzyl, α-(t-butoxycarbonylamino)-4-trifluoromethylbenzyl, α-formyloxy-4-methylbenzyl, α-benzyloxycarbonyl-3-n-butylbenzyl, α-(benzyloxycarbonylamino)-4-methoxybenzyl, α-formyloxy-3-ethoxybenzyl, and the like.

Of the above, it is highly preferred that R is

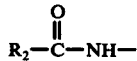

and that $R_2$ thereof is $R'-(O)_m-CH_2-$ in which R' is phenyl.

In portions of the definition provided herein for the group $R_2$, the terms "protected amino", "protected hydroxy", and "protected carboxy" are employed.

The term "protected amino", when employed herein, refers to an amino group substituted with one of the commonly employed amino blocking groups such as t-butyloxycarbonyl (t-BOC), benzyloxycarbonyl, 4-methoxybenzyloxycarbonyl, 4-nitrobenzyloxycarbonyl, 2,2,2-trichloroethoxycarbonyl, diphenylmethoxycarbonyl, isobutyloxycarbonyl, cyclopentyloxycarbonyl, cyclohexyloxycarbonyl, chloroacetyl, dichloroacetyl, 2-chloropropionyl, 3-phenylpropionyl, 4-chlorobutyryl, benzyl, trityl, and the like. Additional typical amino protecting groups are described by J. W. Barton in *Protective Groups in Organic Chemistry*, by J. F. W. McOmie, Ed., Plenum Press, New York, N.Y., 1973, Chapter 2. Any of these are recognized as useful within the meaning of the term "protected amino" employed herein.

The term "protected hydroxy", when employed herein, refers to the readily cleavable groups formed with an hydroxyl group such as formyloxy, chloroacetoxy, benzyloxy, benzhydryloxy, trityloxy, 4-nitrobenzyloxy, and the like. Other hydroxy protecting groups, including those described by C. B. Reese in *Protective Groups in Organic Chemistry*, supra, Chapter 3, are considered to be within the term "protected hydroxy" as used herein.

The term "protected hydroxy", when employed herein, refers to a carboxy group which has been protected by one of the commonly used carboxylic acid protecting groups employed to block or protect the carboxylic acid functionality of a compound while a reaction or sequence of reactions involving other functional sites of the compound are carried out. Such protected carboxy groups are noted for their ease of cleavage to the corresponding carboxylic acid by hydrolytic or by hydrogenolytic methods. Any of those groups defined hereinabove for $R_1$ are also included within the meaning of the term "protected carboxy". Examples of carboxylic acid protecting groups include t-butyl, benzyl, 4-methoxybenzyl, $C_2$-$C_6$ alkanoyloxymethyl, 2-iodoethyl, 4-nitrobenzyl, diphenylmethyl (benzhydryl), phenacyl, p-halophenacyl, 2,2,2-trichloroethyl, succinimidomethyl, and like ester forming moieties. The nature of such ester forming groups is not critical; it is preferred, however, that the ester formed therewith be stable under the reaction conditions of the process of this invention. Furthermore, other known carboxy protecting groups such as those described by E. Haslam in *Protective Groups in Organic Chemistry*, supra, Chapter 5, are considered to be within the term "protected carboxy" as used herein.

Preferred groups within the term "protected carboxy" are tert-butyl, 4-methoxybenzyl, 4-nitrobenzyl, benzhydryl, and 2,2,2-trichloroethyl.

In the foregoing definitions, hydroxy, amino, and carboxy protecting groups, of course, are not exhaustively described. The purpose of these groups is to protect reactive functional groups during preparation of a desired product. They then are removed without disruption of the remainder of the molecule. Many such protecting groups are well known in the art, and their use is equally applicable in the process of this invention.

In addition, the group R in the process of this invention can be an imidazolidinyl group of the formula

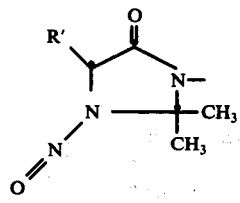

in which R' is phenyl or phenyl substituted with 1 or 2 halogens, protected hydroxy, nitro, cyano, trifluoromethyl, $C_1$–$C_4$ alkyl, or $C_1$–$C_2$ alkoxy.

R' in the above imidazolidinyl formula typically includes phenyl, 3-bromophenyl, 2-chlorophenyl, 4-fluorophenyl, 3-iodophenyl, 3-chloro-4-fluorophenyl, 2-chloro-4-bromophenyl, 4-formyloxyphenyl, 3-formyloxyphenyl, 4-nitrophenyl, 2-cyanophenyl, 3-trifluoromethylphenyl, 4-methylphenyl, 3-ethylphenyl, 4-isopropylphenyl, 4-t-butylphenyl, 3-methoxyphenyl, 2-ethoxyphenyl, 4-methoxyphenyl, and the like.

Compounds in which R is the aforedescribed imidazolidinyl group can be prepared in accordance with known techniques by reacting a compound in which R is

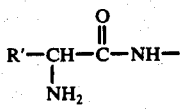

with acetone under moderately basic conditions to produce the corresponding compound in which R is a labile intermediate of the formula

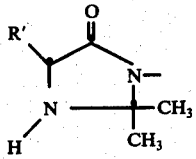

This product then is converted to the stable N-nitroso derivative in which R is the aforedescribed imidazolidinyl group. The latter conversion is accomplished by treatment of the intermediate with sodium nitrite under acidic conditions and with cooling.

In the process of this invention the 3-hydroxy cephalosporins are prepared by ring-closure of a butenoate ester of the formula

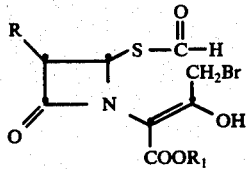

The butenoate ester starting materials are available by reaction of the corresponding 3-bromomethyl-$\Delta^2$-cephem compounds of the formula

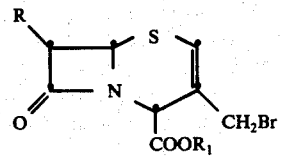

with ozone to form an intermediate ozonide which then is decomposed to the butenoate ester by treatment with a mild reducing agent. The 3-bromomethyl-$\Delta^2$-cephem compounds, in turn, are available from the process disclosed in the Webber et al. U.S. Pat. No. 3,637,678 by reaction of a 3-methyl-$\Delta^2$-cephem with N-bromosuccinimide.

Stated more particularly, a 7-amido(or imido)-3-bromomethyl-2-cephem-4-carboxylic acid ester is ozonolyzed by reaction with ozonized oxygen, to form an intermediate ozonide at the $C_2$–$C_3$ double bond of the $\Delta^2$-cephem. Treatment of the ozonide so formed with a mild reducing agent effects decomposition of the ozonide and provides the butenoate ester starting material corresponding in structure to the 3-bromomethyl-$\Delta^2$-cephem precursor. The ozonolysis of the 3-bromomethyl-$\Delta^2$-cephem generally is carried out by passing ozonized oxygen gas through a solution of the 3-bromomethyl-$\Delta^2$-cephem in an inert solvent. The reaction generally is carried out at a temperature below about 0° C., and typically at a temperature of from about $-100°$ C. to about $-40°$ C. Of those reactive moieties of the $\Delta^2$-cephem, the $C_2$–$C_3$ double bond preferentially reacts with the ozone to form, in situ, an intermediate ozonide. Generally, the ozonide is not isolated; instead, it is decomposed while in the reaction mixture to provide the butenoate ester. At least a stoichiometric amount of ozone gas generally is employed, although a moderate excess of the ozone, typically an excess of from about 0.1 to about 1 on a molar basis, can be utilized if desired. A large excess of ozone should be avoided, however, since over-oxidation of the cephem can occur. For example, the sulphur atom of the cephem ring system can react with the ozone to form the corresponding sulfoxide. Although sulfoxide formation can occur in the presence of a large excess of ozone, such oxidation proceeds at a very slow rate, and, thus, reaction of the $C_2$–$C_3$ cephem double bond with ozone occurs preferentially and usually proceeds very rapidly. The progress of the ozonolysis reaction generally is monitored to determine the relative amounts of the starting 3-bromomethyl-$\Delta^2$-cephem and the corresponding ozonide product present in the reaction mixture. For instance, the progress of the desired oxidation can be monitored chromatographically by withdrawing an aliquot portion of the reaction mixture, decomposing the intermediate ozonide by adding to the aliquot portion an amount of a mild reducing agent, and chromatographing the aliquot solution by thin layer chromatography. The amount of unreacted 3-bromomethyl-$\Delta^2$-cephem remaining in the reaction mixture can be assessed by comparison of the thin layer chromatogram with that of the amount of 3-bromomethyl-$\Delta^2$-cephem present in an aliquot at the outset of the ozonolysis. The ozonolysis reaction generally is curtailed when no starting $\Delta^2$-cephem remains in the reaction mixture, thereby minimizing the possibilities for over-oxidation. Generally, the ozonolysis is substantially completed within 1 to 5 hours. As hereinbefore indicated, the ozonolysis reaction is best conducted in an inert solvent. Any of a number of inert solvents can be employed for the reaction. Commonly used inert solvents include the halogenated hydrocarbons, such as chloroform, dichloromethane, fluorotrichloromethane, 1,2-dichloroethane, dichlorodifluoromethane, 1,1-dichloroethane, bromoethane, carbon tetrachloride, and the like. Additionally, ethers such as diethyl ether, petroleum ether, tetrahydrofuran, diethylene glycol dimethyl ether, methyl ethyl ether, and related ethers are suitable inert solvents. Similarly, solvents such as hexane, dimethylformamide, dimethylacetamide, ethyl acetate, methyl acetate, water, acetic acid, and the like, can be employed in the ozonolysis reaction.

Upon completion of the ozonolysis reaction, as evidenced, for example, by the lack of any 3-bromomethyl-$\Delta^2$-cephem remaining in the reaction mixture as shown by thin layer chromatographic analysis, any excess ozone remaining in the reaction mixture generally is removed by purging the reaction mixture with nitrogen or oxygen gas. The ozonide intermediate which is formed by ozonolysis of the Δ²-cephem need not be isolated; instead, it is decomposed by reaction with a mild reducing agent to provide the butenoate ester starting material.

The term "mild reducing agent" refers to any reducing agent capable of decomposing the ozonide intermediate while at the same time not affecting other sites of the ozonide molecular. For example, the reducing agent must not hydrolyze the azetidinone ring system of the butenoate ester under the reaction conditions being used. Mild reducing agents which are commonly used to decompose ozonides are well known, and include such agents as zinc or magnesium and water or acetic acid, sodium bisulfite, sulfur dioxide, trimethyl phosphite, stannous chloride, zinc metal dust, Raney nickel, and the like. The decomposition of the intermediate ozonide normally is accomplished by adding an excess of the reducing agent to the reaction mixture maintained at a temperature of from about −80° C. to about 0° C. and stirring the mixture. The ozonide decomposition generally is completed within about 1 to 3 hours. Progress of the decomposition can be monitored by periodically treating a sample of the reaction mixture with a potassium iodide-starch mixture.

The butenoate ester typically is isolated by washing the reaction mixture with water, separating the organic phase, and concentrating it to dryness. The product can be further purified, if desired, by any of a number of commonly used purification techniques, including column chromatography, gas chromatography, recrystallization, and related methods.

If, of course, will be understood by those skilled in the art of organic chemistry that the butenoate ester starting materials are enols and exist in tautomeric equilibrium with the corresponding 1,3-dicarbonyl ketone. The tautomeric equlibrium can be illustrated by the following generalized scheme:

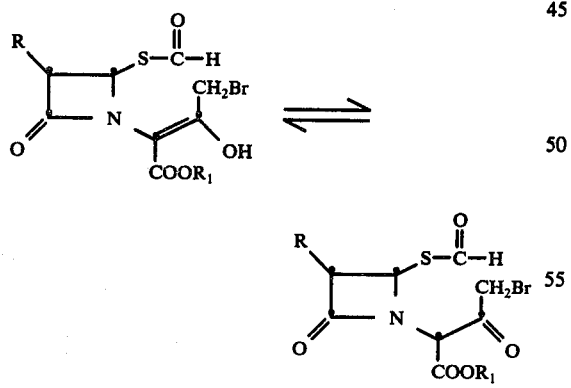

As a result of the existence of this tautomeric equilibrium, the keto form of the molecule will be understood to be included in the definition of the butenoate ester starting material.

By the process of this invention, the butenoate ester starting material is ring-closed by reaction with DBN or DBU. DBN is the shorthand expression for 1,5-diazabicyclo[4.3.0]non-5-ene which has the formula

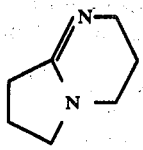

DBU is the shorthand expression for 1,5-diazabicyclo[5.4.0]undec-5-ene which has the formula

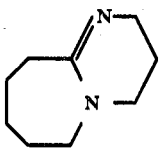

In carrying out the process of this invention, the butenoate ester typically is mixed with at least a molar equivalent of DBN or DBU and preferably from about a molar equivalent to about a 10% excess on a molar basis of the DBN or DBU relative to the butenoate ester.

The butenoate ester and the DBN or the DBU generally are dissolved in a suitable inert organic solvent. Any of a host of solvents can be employed as long as they are inert under the conditions at which the ring-closure is carried out. Preferred inert organic solvents include a halogenated hydrocarbon, for example, methylene chloride, chloroform, carbon tetrachloride, 1,1,2-trichloroethane, and the like.

The preparation of a 3-hydroxy cephalosporin in accordance with the process of this invention typically is accomplished by treating the aforedescribed mixture of reactants and solvent at a temperature of from about 0° C. to about +25° C., and preferably from about +20° C. to about +25° C., for a period of from about 15 minutes to about 1 hour. The reaction generally is quite rapid. Nevertheless, the reaction time can be greatly extended, even to several hours; however, any extended period of reaction may be accompanied by substantial loss of or serious detriment to the ultimate 3-hydroxy cephalosporin product which is formed.

Generally, isolation of the 3-hydroxycephalosporin product can be accomplished by simple filtration of the reaction mixture upon completion of reaction time. The product normally will precipitate from the mixtur as it is formed and thus is readily isolable.

In the event that the 3-hydroxycephalosporin product does not precipitate from the reaction mixture, the product can be isolated by washing the reaction mixture with dilute acid to effect removal of any remaining DBN or DBU. The organic mixture then is washed with water followed by aqueous brine and then is evaporated to obtain the product as a residue.

If desired, the 3-hydroxycephalosporin product can be further purified by any of a number of commonly used purification techniques, including column chromatography, gas chromatography, recrystallization, and related methods.

Examples of the conversions which are available from the process of this invention are the following:

t-butyl 3-hydroxy-4-bromo-2-(2-formylthio-4-oxo-3-phthalimido-1-azetidinyl)-2-butenoate to t-butyl 7-phthalimido-3-hydroxy-3-cephem-4-carboxylate;

benzyl 3-hydroxy-4-bromo-2-(2-formylthio-4-oxo-3-formamido-1-azetidinyl)-2-butenoate to benzyl 7-formamido-3-hydroxy-3-cephem-4-carboxylate;

2,2,2-trichloroethyl 3-hydroxy-4-bromo-2-(2-formylthio-4-oxo-3-acetamido-1-azetidinyl)-2-butenoate to 2,2,2-trichloroethyl 7-acetamido-3-hydroxy-3-cephem-4-carboxylate;

p-nitrobenzyl 3-hydroxy-4-bromo-2-(2-formylthio-4-oxo-3-butyramido-1-azetidinyl)-2-butenoate to p-nitrobenzyl 7-butyramido-3-hydroxy-3-cephem-4-carboxylate;

p-methoxybenzyl 3-hydroxy-4-bromo-2-(2-formylthio-4-oxo-3-chloroacetamido-1-azetidinyl)-2-butenoate to p-methoxybenzyl 7-chloroacetamido-3-hydroxy-3-cephem-4-carboxylate;

benzhydryl 3-hydroxy-4-bromo-[2-formylthio-4-oxo-3-(4'-chloroacetamido-4'-benzhydryloxycarbonyl-valeramido)-1-azetidinyl]-2-butenoate to benzhydryl 7-(4'-chloroacetamido-4'-benzhydryloxycarbonyl-valeramido)-3-hydroxy-3-cephem-4-carboxylate;

p-nitrobenzyl 3-hydroxy-4-bromo-2-[2-formylthio-4-oxo-3-(4'-nitrobenzyloxycarbamido)-1-azetidinyl]-2-butenoate to p-nitrobenzyl 7-(4'-nitrobenzyloxycarbamido)-3-hydroxy-3-cephem-4-carboxylate;

t-amyl 3-hydroxy-4-bromo-2-(2-formylthio-4-oxo-3-benzyloxycarbamido-1-azetidinyl)-2-butenoate to t-amyl 7-benzyloxycarbamido-3-hydroxy-3-cephem-4-caboxylate;

ethyl 3-hydroxy-4-bromo-2-[2-formylthio-4-oxo-3-(t-butyloxycarbamido)-1-azetidinyl]-2-butenoate to ethyl 7-(t-butyloxycarbamido)-3-hydroxy-3-cephem-4-carboxylate;

2-iodoethyl 3-hydroxy-4-bromo-2-[2-formylthio-4-oxo-3-(2',2',2'-trichloroethoxycarbamido)-1-azetidinyl]-2-butenoate to 2-iodoethyl 7-(2',2',2'-trichloroethoxycarbamido)-3-hydroxy-3-cephem-4-carboxylate;

acetoxymethyl 3-hydroxy-4-bromo-2-[2-formylthio-4-oxo-3-(4'-methoxybenzyloxycarbamido)-1-azetidinyl]-2-butenoate to acetoxymethyl 7-(4'-methoxybenzyloxycarbamido)-3-hydroxy-3-cephem-4-carboxylate;

p-methoxybenzyl 3-hydroxy-4-bromo-2-(2-formylthio-4-oxo-3-phenylacetamido-1-azetidinyl)-2-butenoate to p-methoxybenzyl 7-phenylacetamido-3-hydroxy-3-cephem-4-carboxylate;

2,2,2-trichloroethyl 3-hydroxy-4-bromo-2-(2-formylthio-4-oxo-3-phenoxyacetamido-1-azetidinyl)-2-butenoate to 2,2,2-trichloroethyl 7-phenoxyacetamido-3-hydroxy-3-cephem-4-carboxylate;

p-nitrobenzyl 3-hydroxy-4-bromo-2-[2-formylthio-4-oxo-3-(2',5'-dichlorophenylacetamido)-1-azetidinyl]-2-butenoate to p-nitrobenzyl 7-(2',5'-dichlorophenylacetamido)-3-hydroxy-3-cephem-4-carboxylate;

benzyl 3-hydroxy-4-bromo-2-[2-formylthio-4-oxo-3-(3'-bromophenoxyacetamido)-1-azetidinyl]-2-butenoate to benzyl 7-(3'-bromophenoxyacetamido)-3-hydroxy-3-cephem-4-carboxylate;

t-butyl 3-hydroxy-4-bromo-2-[2-formylthio-4-oxo-3-(4'-chloroacetoxyphenylacetamido)-1-azetidinyl]-2-butenoate to t-butyl 7-(4'-chloroacetoxyphenylacetamido)-3-hydroxy-3-cephem-4-carboxylate;

t-hexyl 3-hydroxy-4-bromo-2-[2-formylthio-4-oxo-3-(3'-formyloxyphenoxyacetamido)-1-azetidinyl]-2-butenoate to t-hexyl 7-(3'-formyloxyphenoxyacetamido)-3-hydroxy-3-cephem-4-carboxylate;

p-nitrobenzyl 3-hydroxy-4-bromo-2-[2-formylthio-4-oxo-3-(2'-nitrophenylacetamido)-1-azetidinyl]-2-butenoate to p-nitrobenzyl 7-(2'-nitrophenylacetamido)-3-hydroxy-3-cephem-4-carboxylate;

p-methoxybenzyl 3-hydroxy-4-bromo-[2-formylthio-4-oxo-3-(4'-nitrophenoxyacetamido)-1-azetidinyl]-2-butenoate to p-methoxybenzyl 7-(4'-nitrophenoxyacetamido)-3-hydroxy-3-cephem-4-carboxylate;

benzhydryl 3-hydroxy-4-bromo-[2-formylthio-4-oxo-3-(3'-cyanophenylacetamido)-1-azetidinyl]-2-butenoate to benzhydryl 7-(3'-cyanophenylacetamido)-3-hydroxy-3-cephem-4-carboxylate;

p-bromophenacyl 3-hydroxy-4-bromo-2-[2-formylthio-4-oxo-3-(2'-cyanophenoxyacetamido)-1-azetidinyl]-2-butenoate to p-bromophenacyl 7-(2'-cyanophenoxyacetamido)-3-hydroxy-3-cephem-4-carboxylate;

propionoxymethyl 3-hydroxy-4-bromo-2-[2-formylthio-4-oxo-3-(4'-trifluoromethylphenylacetamido)-1-azetidinyl]-2-butenoate to propionoxymethyl 7-(4'-trifluoromethylphenylacetamido)-3-hydroxy-3-cephem-4-carboxylate;

2,2,2-tribromoethyl 3-hydroxy-4-bromo-2-[2-formylthio-4-oxo-3-(3'-trifluoromethylphenoxyacetamido)-1-azetidinyl]-2-butenoate to 2,2,2-tribromoethyl 7-(3'-trifluoromethylphenoxyacetamido)-3-hydroxy-4-carboxylate;

2-iodoethyl 3-hydroxy-4-bromo-2-[2-formylthio-4-oxo-3-(2'-ethylphenylacetamido)-1-azetidinyl]-2-butenoate to 2-iodoethyl 7-(2'-ethylphenylacetamido)-3-hydroxy-3-cephem-4-carboxylate;

acetoxymethyl 3-hydroxy-4-bromo-2-[2-formylthio-4-oxo-3-(4'-isopropylphenoxyacetamido)-1-azetidinyl]-2-butenoate to acetoxymethyl 7-(4'-isopropylphenoxyacetamido)-3-hydroxy-3-cephem-4-carboxylate;

t-butyl 3-hydroxy-4-bromo-2-[2-formylthio-4-oxo-3-(3'-ethoxyphenylacetamido)-1-azetidinyl]-2-butenoate to t-butyl 7-(3'-ethoxyphenylacetamido)-3-hydroxy-3-cephem-4-carboxylate;

p-nitrobenzyl 3-hydroxy-4-bromo-2-[2-formylthio-4-oxo-3-(4'-methoxyphenoxyacetamido)-1-azetidinyl]-2-butenoate to p-nitrobenzyl 7-(4'-methoxyphenoxyacetamido)-3-hydroxy-3-cephem-4-carboxylate;

p-nitrobenzyl 3-hydroxy-4-bromo-2-[2-formylthio-4-oxo-3-(α-formyloxyphenylacetamido)-1-azetidinyl]-2-butenoate to p-nitrobenzyl 7-(α-formyloxyphenylacetamido)-3-hydroxy-3-cephem-4-carboxylate;

p-methoxybenzyl 3-hydroxy-4-bromo-2-[2-formylthio-4-oxo-3-(α-benzhydryloxyphenylacetamido)-1-azetidinyl]-2-butenate to p-methoxybenzyl 7-(α-benzhydryloxyphenylacetamido)-3-hydroxy-3-cephem-4-carboxylate;

benzhydryl 3-hydroxy-4-bromo-2-[2-formylthio-4-oxo-3-(α-benzhydryloxycarbonylphenylacetamido)-1-azetidinyl]-2-butenoate to benzhydryl 7-(α-benzhydryloxyphenylacetamido)-3-hydroxy-3-cephem-4-carboxylate;

p-nitrobenzyl 3-hydroxy-4-bromo-2-[2-formylthio-4-oxo-3-(α-benzyloxycarbonylaminophenylacetamido)-1-azetidinyl]-2-butenoate to p-nitrobenzyl 7-(α-benzyloxycarbonylaminophenylacetamido)-3-hydroxy-3-cephem-4-carboxylate;

t-butyl 3-hydroxy-4-bromo-2-[2-formylthio-4-oxo-3-(α-t-butyloxycarbonylaminophenylacetamido)-1-azetidinyl]-2-butenoate to t-butyl 7-(α-t-butyloxycarbonylaminophenylacetamido)-3-hydroxy-3-cephem-4-carboxylate;

p-nitrobenzyl 3-hydroxy-4-bromo-2-[2-formylthio-4-oxo-3-(2'-thienylacetamido)-1-azetidinyl]-2-butenoate to p-nitrobenzyl 7-(2'-thienylacetamido)-3-hydroxy-3-cephem-4-carboxylate;

and the like.

The 3-hydroxy cephalosporins (3-hydroxycephems) obtained from the process of this invention can be employed in the preparation of cephem antibiotics of the formula

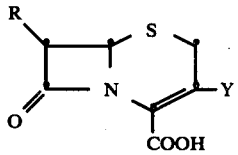

in which Y is, for example, chloro, bromo or methoxy. Such chemical conversions from 3-hydroxy cephalosporin compounds have been disclosed in the chemical literature [Robert R. Chauvette and Pamela A. Pennington, *Journal of the American Chemical Society*, 96, 4986 (1974)].

In general, the 3-hydroxycephems can be treated with diazomethane at room temperature in tetrahydrofuran containing one equivalent of triethylamine to produce the corresponding 3-methoxycephem derivatives. The 3-halocephems are derived from the 3-hydroxycephem esters by treatment with a halogenating reagent such as thionyl chloride or phosphorus tribromide in N,N-dimethylformamide.

The corresponding cephem acids exhibit potent antibacterial activity. These are available by cleavage of the ester function. Deesterification can be achieved, depending on the nature of the protecting group, by any of several recognized procedures, including (1) treatment with an acid such as trifluoroacetic acid, formic acid, hydrochloric acid or the like; (2) treatment with zinc and an acid such as formic acid, acetic acid or hydrochloric acid; or (3) hydrogenation in the presence of palladium, platinum, rhodium or a compound thereof, in suspension, or on a carrier such as barium sulfate, carbon, alumina, or the like.

This invention is further illustrated by reference to the examples which follow. It is not intended that this invention be limited in scope by reason of any of the examples provided herein.

EXAMPLE 1

A solution of 1.932 g. (4 mmoles) of t-butyl-7-phenoxyacetamido-3-bromomethyl-2-cephem-4-carboxylate and 100 ml. of $CH_2Cl_2$ was cooled in an acetone — dry ice bath ($-78°$ C.), and ozone was introduced until a blue color appeared (about 3–5 minutes). Sulfur dioxide gas then was passed through the mixture for about 2–5 minutes, and the mixture was allowed to warm to room temperature. An nmr analysis of a sample of the mixture was consistent for the presence of t-butyl 3-hydroxy-4-bromo-2-(2-formylthio-4-oxo-3-phenoxyacetamido-1-azetidinyl)-2-butenoate.

NMR ($CDCl_3$ $\delta$ 1.5 (s, t-Bu), 4.1 and 4.3 (dd, J = 12 Hz, $CH_2Br$), 4.53 (s, $CH_2O$), 5.15 and 5.35 (dd, J = 5 Hz), 6.1 (d, J = 5 Hz), 6.8 – 7.3 (m, 5 arom. H), 7.45 (d, NH), 10 (s, CHO), and 12.4 Hz (br. s, OH)

To the reaction mixture than was added 0.5 ml. of 1,5-diazabicyclo[3.4.0]non-5-ene (DBN). A precipitate immediately formed. The mixture was maintained at room temperature for about 30 minutes and then was filtered. The recovered crude product was chromatographed over silica gel using a mixture of toluene and ethyl acetate to obtain t-butyl 7-phenoxyacetamido-3-hydroxy-3-cephem-4-carboxylate containing some butenoate ester starting material.

NMR ($CDCl_3$) $\delta$ 3.23 and 3.4 (dd, $CH_2S$, J = 12 Hz), 4.6 (s, $CH_2O$), 5.1 (d, 6-H, J = Hz), 5.65 and 5.95 (dd, 7-H, J = 5 Hz), 6.8 –8.4 (m, 5 arom. H), and 11.5 Hz (br. s, OH).

EXAMPLE 2

A solution of 2.36 g. (4 mmoles) of p-nitrobenzyl 7-α-formyloxyphenylacetamido-3-bromomethyl-2-cephem-4-carboxylate and 100 ml. of chloroform is cooled in an acetone — dry ice bath ($-78°$ C.), and ozone is introduced until a blue color appears (about 3–5 minutes). Sulfur dioxide gas then is passed through the mixture for about 2–5 minutes, and the mixture is allowed to warm to room temperature. An analysis of a sample of the mixture is consistent for p-nitrobenzyl 3-hydroxy-4-bromo-2-(2-formylthio-4-oxo-3-α-formyloxyphenylacetamido-1-azetidinyl)-2-butenoate.

To the reaction mixture then is added 1.0 ml. of 1,5-diazabicyclo[5.4.0]undec-5-ene (DBU). The mixture is maintained at room temperature for about 30 minutes. The mixture then is washed successively with 1N HCl, water, and brine. The organic layer is evaporated, and the recovered crude product is chromatographed over silica gel to obtain p-nitrobenzyl 7-α-formyloxyphenylacetamido-3-hydroxy-3-cephem-4-carboxylate.

EXAMPLE 3

A solution of 1.36 g. (2 mmoles) of p-methoxybenzyl 7-(α-benzyloxycarbonylamino)phenylacetamido-3-bromomethyl-2-cephem-4-carboxylate and 60 ml. of chloroform is cooled in an acetone — dry ice bath ($-78°$ C.), and ozone is introduced until a blue color appears (about 2–3 minutes). Sulfur dioxide gas then is passed through the mixture for about 3 minutes, and the mixture is allowed to warm to room temperature. An analysis of a sample of the mixture is consistent for p-methoxybenzyl 3-hydroxy-4-bromo-2-[2-formylthio-4-oxo-3-(α-benzyloxycarbonylamino)phenylacetamido-1-azetidinyl]-2-butenoate.

To the reaction mixture then is added 0.4 ml. of 1,5-diazabicyclo[3.4.0]non-5ene (DBN). The mixture is maintained at room temperature for about 45 minutes and then is filtered. The recovered crude product is chromatographed over silica gel to obtain p-methoxybenzyl 7-(α-benzyloxycarbonylamino)-phenylacetamido-3-hydroxy-3-cephem-4-carboxylate.

EXAMPLE 4

A solution of 2.7 g. (5 mmoles) of benzhydryl 7-phenylacetamido-3-bromomethyl-2-cephem-4-carboxylate and 125 ml. of carbon tetrachloride is cooled in an acetone — dry ice bath ($-78°$ C.), and ozone is introduced until a blue color appears (about 5–6 minutes). Sulfur dioxide gas then is passed through the mixture for about 5–7 minutes, and the mixture is allowed to warm to room temperature. An analysis of a sample of the mixture is consistent for benzhydryl 3-hydroxy-4-bromo-2-(2-formylthio-4-oxo-3-phenylacetamido-1-azetidinyl)-2-butenoate.

To the reaction mixture then is added 1.0 ml. of 1,5-diazabicyclo[5.4.0]undec-5-ene (DBU). The mixture is maintained at room temperature for about 60 minutes and then is filtered. The recovered crude product is chromatographed over silica gel to obtain benzhydryl 7-phenylacetamido-3-hydroxy-3-cephem-4-carboxylate.

EXAMPLE 5

A solution of 1.77 g. (3 mmoles) of 2,2,2-trichloroethyl 7-(4'-formyloxyphenylacetamido)-3-bromomethyl-2-cephem-4-carboxylate and 80 ml. of methylene chloride is cooled in an acetone — dry ice bath (−78° C.), and ozone is introduced until a blue color appears (about 5–7 minutes). Sulfur dioxide gas then is passed through the mixture for about 6 minutes, and the mixture is allowed to warm to room temperature. An analysis of a sample of the mixture is consistent for 2,2,2-trichloroethyl 3-hydroxy-4-bromo-2-[2-formylthio-4-oxo-3-(4'-formyloxyphenylaetamido)-1-azetidinyl]-2-butenoate.

To the reaction mixture then is added 0.5 ml. of 1,5-diazabicyclo[3.4.0]non-5-ene (DBN). The mixture is maintained at room temperature for about 15 minutes and then is filtered. The recovered crude product is chromatographed over silica gel to obtain 2,2,2-trichloroethyl 7-(4'-formyloxyphenylacetamido)-3-hydroxy-3-cephem-4-carboxylate.

EXAMPLE 6

A solution of 5.1 g. (10 mmoles) of benzyl 7-(2'-thienylacetamido)-3-bromomethyl-2-cephem-4-carboxylate and 200 ml. of methylene chloride is cooled in an acetone — dry ice bath (−78° C.), and ozone is introduced until a blue color appears (about 8–10 minutes). Sulfur dioxide gas then is passed through the mixture for about 10 minutes, and the mixture is allowed to warm to room temperature. An analysis of a sample of the mixture is consistent for benzyl 3-hydroxy-4-bromo-2-[2-formylthio-4-oxo-3-(2'-thienylacetamido)-1-azetidinyl]-2-butenoate.

To the reaction mixture then is added 1.5 ml. of 1,5-diazabicyclo[5.4.0]undec-5-ene (DBU). The mixture is maintained at room temperature for about 60 minutes and then is filtered. The recovered crude product is chromatographed over silica gel to obtain benzyl 7-(2'-thienylacetamido)-3-hydroxy-3-cephem-4-carboxylate.

EXAMPLE 7

A solution of 1.59 g. (3 mmoles) of acetoxymethyl 7-(3'-chlorophenoxyacetamido)-3-bromomethyl-2-cephem-4-carboxylate and 70 ml. of methylene chloride is cooled in an acetone — dry ice bath (−78° C.), and ozone is introduced until a blue color appears (about 3–5 minutes). Sulfur dioxide gas then is passed through the mixture for about 2–5 minutes, and the mixture is allowed to warm to room temperature. An analysis of a sample of the mixture is consistent for acetoxymethyl 3-hydroxy-4-bromo-2-[2-formylthio-4-oxo-3-(3'-chlorophenoxyacetamido)-1-azetidinyl]-2-butenoate.

To the reaction mixture then is added 0.8 ml. of 1,5-diazacyclo[5.4.0]undec-5-ene (DBU). The mixture is maintained at room temperature for about 20 minutes and then is filtered. The recovered crude product is chromatographed over silica gel to obtain acetoxymethyl 7-(3'-chlorophenoxyacetamido)-3-hydroxy-3-cephem-4-carboxylate.

EXAMPLE 8

A solution of 3.85 g. (5 mmoles) of p-nitrobenzyl 7-(α-benzhydryloxycarbonylphenylacetamido)-3-bromomethyl-2-cephem-4-carboxylate and 170 ml. of methylene chloride is cooled in an acetone — dry ice bath (−78° C.), and ozone is introduced until a blue color appears (about 5–7 minutes). Sulfur dioxide gas then is passed through the mixture for about 6–8 minutes, and the mixture is allowed to warm to room temperature. An analysis of a sample of the mixture is consistent for p-nitrobenzyl 3-hydroxy-4-bromo-2-[2-formylthio-4-oxo-3-(α-benzhydryloxycarbonylphenylacetamido)-1-azetidinyl]-2-butenoate.

To the reaction mixture then is added 0.9 ml. of 1,5-diazabicyclo[3.4.0]non-5-ene (DBN). The mixture is maintained at room temperature for about 15 minutes and then is filtered. The recovered crude product is chromatographed over silica gel to obtain p-nitrobenzyl 7-(α-benzhydryloxycarbonyl)-phenylacetamido-3-hydroxy-3-cephem-4-carboxylate.

We claim:
1. A process for preparing a 3-hydroxycephalosporin of the formula

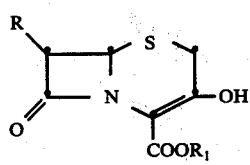

which comprises reacting a compound of the formula

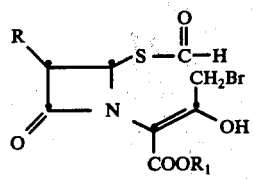

with an amine selected from the group consisting of 1,5-diazabicyclo[5.4.0]undec-5-ene and 1,5-diazabicyclo[3.4.0]non-5-ene at a temperature of from about 0° C. to about 25° C., in which, in the above formulae, $R_1$ is a carboxylic acid protecting group, and R is
  a. phthalimido,
  b. an amido group of the formula

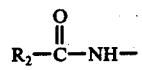

in which $R_2$ is
  1. hydrogen, $C_1$–$C_3$ alkyl, halomethyl, thienyl-2-methyl, 4-protected-amino-4-protected carboxybutyl, benzyloxy, 4-nitrobenzyloxy, t-butyloxy, 2,2,2-trichloroethoxy, 4-methoxybenzyloxy;
  2. a group of the formula $R'—(O)_m—CH_2—$ in which $m$ is 0 or 1, and $R'$ is phenyl or phenyl substituted with 1 or 2 halogens, protected hydroxy, nitro, cyano, trifluoromethyl, $C_1$–$C_4$ alkyl, or $C_1$–$C_2$ alkoxy;
  3. a group of the formula

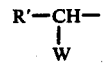

in which R' is as defined above and W is protected hydroxy, protected carboxy, or protected amino; or
  c. an imidazolidinyl group of the formula

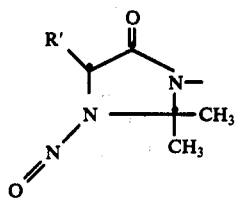

in which R' is as defined above.

2. Process of claim 1, in which $R_1$ is $C_4$–$C_6$ tert-alkyl, 2,2,2-trihaloethyl, 2-iodoethyl, benzyl, p-nitrobenzyl, succinimidomethyl, phthalimidomethyl, p-methoxybenzyl, benzhydryl, $C_2$–$C_6$ alkanoyloxymethyl, phenacyl, or p-halophenacyl.

3. Process of claim 2, in which $R_1$ is t-butyl, benzyl, p-nitrobenzyl, p-methoxybenzyl, benzhydryl, or 2,2,2-trichloroethyl.

4. Process of claim 1, in which R is an amido group of the formula

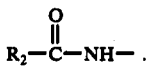

5. Process of claim 4, in which $R_2$ is a group of the formula $R'—(O)_m—CH_2—$.

6. Process of claim 5, in which R' is phenyl.

7. Process of claim 4, in which $R_2$ is a group of the formula

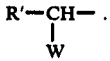

8. Process of claim 1, in which the reaction is carried out in the presence of an inert organic solvent.

9. Process of claim 1, in which the reaction is carried out at a temperature of from about +20° C. to about +25° C.

10. Process of claim 9, in which the reaction is carried out for a period of from about 15 minutes to about 1 hour.

* * * * *